(12) United States Patent
Sandhu

(10) Patent No.: US 9,918,709 B2
(45) Date of Patent: *Mar. 20, 2018

(54) STAND-ALONE ACCESS SYSTEM FOR MINIMALLY INVASIVE SPINAL SURGERY

(71) Applicant: Spinal USA, Inc., Parsippany, NJ (US)

(72) Inventor: Faheem A. Sandhu, Washington, DC (US)

(73) Assignee: Spinal USA, Inc., Parsippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/235,765

(22) Filed: Aug. 12, 2016

(65) Prior Publication Data

US 2017/0156716 A1    Jun. 8, 2017

Related U.S. Application Data

(60) Continuation of application No. 14/665,438, filed on Mar. 23, 2015, now Pat. No. 9,414,831, which is a division of application No. 13/858,976, filed on Apr. 9, 2013, now Pat. No. 8,986,344, which is a division of application No. 11/164,831, filed on Dec. 7, 2005, now Pat. No. 8,480,576.

(51) Int. Cl.
| | | |
|---|---|---|
| *A61B 17/02* | (2006.01) | |
| *A61B 1/07* | (2006.01) | |
| *A61B 1/32* | (2006.01) | |
| *A61B 17/34* | (2006.01) | |
| *A61M 29/00* | (2006.01) | |
| *A61B 17/00* | (2006.01) | |

(52) U.S. Cl.
CPC ............ *A61B 17/0218* (2013.01); *A61B 1/07* (2013.01); *A61B 1/32* (2013.01); *A61B 17/3423* (2013.01); *A61M 29/00* (2013.01); *A61B 2017/0046* (2013.01); *A61B 2017/0256* (2013.01); *A61M 2210/1003* (2013.01)

(58) Field of Classification Search
CPC ............................. A61B 17/02; A61B 17/0218
See application file for complete search history.

(56) References Cited

U.S. PATENT DOCUMENTS

| | | | |
|---|---|---|---|
| 1,894,061 A * | 1/1933 | Sanders | ............... A63H 33/084 |
| | | | 446/114 |
| 2,691,242 A | 10/1954 | Young | |
| 3,965,890 A | 6/1976 | Gauthier | |

(Continued)

OTHER PUBLICATIONS

Le, Hoang MD et al., "Clinical outcomes after minimal-access surgery for recurrent lumbar disc herniation", Neurosurg Focus 15(3):Article 12 2003 vol. 15 Sep. 2003, pp. 1-4.

(Continued)

*Primary Examiner* — Christian Sevilla
(74) *Attorney, Agent, or Firm* — Knobbe, Martens, Olson & Bear, LLP

(57) ABSTRACT

A retractor assembly for defining a working channel to a surgical site for conducting minimally invasive spinal surgery includes a plurality of relatively articulable components. Temporary interconnections are formed between adjacent sidewalls of the components to hold the components in a desired configuration, such as in a closed triangular form. The components are articulable relative to each other for adjusting the working channel or for performing surgical functions.

8 Claims, 23 Drawing Sheets

(56) References Cited

U.S. PATENT DOCUMENTS

| | | | |
|---|---|---|---|
| 4,747,394 A | | 5/1988 | Watanabe |
| 4,817,587 A | * | 4/1989 | Janese ............... A61B 17/0293 |
| | | | 600/210 |
| 5,307,805 A | * | 5/1994 | Byrne ............... A61B 17/0218 |
| | | | 600/214 |
| 5,772,661 A | | 6/1998 | Michelson |
| 5,928,139 A | * | 7/1999 | Koros ............... A61B 17/0206 |
| | | | 600/205 |
| 5,944,658 A | | 8/1999 | Koros et al. |
| 5,954,635 A | | 9/1999 | Foley et al. |
| 6,109,329 A | | 8/2000 | Russo |
| 6,139,493 A | | 10/2000 | Koros et al. |
| 6,206,826 B1 | | 3/2001 | Mathews et al. |
| 6,312,443 B1 | | 11/2001 | Stone |
| 6,360,750 B1 | | 3/2002 | Gerber et al. |
| 6,425,859 B1 | | 7/2002 | Folev et al. |
| 6,520,907 B1 | | 2/2003 | Foley et al. |
| 6,800,084 B2 | | 10/2004 | Davison et al. |
| 6,837,891 B2 | | 1/2005 | Davison et al. |
| 6,945,933 B2 | | 9/2005 | Branch et al. |
| 6,951,538 B2 | | 10/2005 | Ritland |
| 7,108,705 B2 | | 9/2006 | Davison et al. |
| 7,207,949 B2 | | 4/2007 | Miles et al. |
| 7,261,688 B2 | | 8/2007 | Smith et al. |
| 7,470,236 B1 | | 12/2008 | Kelleher et al. |
| 7,473,222 B2 | | 1/2009 | Dewey et al. |
| 7,513,869 B2 | | 4/2009 | Branch et al. |
| 7,524,285 B2 | | 4/2009 | Branch et al. |
| 7,582,058 B1 | | 9/2009 | Miles et al. |
| 7,691,057 B2 | | 4/2010 | Miles et al. |
| 7,819,801 B2 | | 10/2010 | Miles et al. |
| 7,981,029 B2 | | 7/2011 | Branch et al. |
| 8,016,767 B2 | | 9/2011 | Miles et al. |
| 8,137,284 B2 | | 3/2012 | Miles et al. |
| 8,343,048 B2 | | 1/2013 | Warren |
| 8,355,780 B2 | | 1/2013 | Miles et al. |
| 8,439,832 B2 | | 5/2013 | Miles et al. |
| 8,480,576 B2 | | 7/2013 | Sandhu |
| 8,986,344 B2 | | 3/2015 | Sandhu |
| 9,259,144 B2 | | 2/2016 | Smith et al. |
| 9,414,831 B2 | | 8/2016 | Sandhu |
| 2001/0011170 A1 | | 8/2001 | Davison et al. |
| 2002/0173798 A1 | | 11/2002 | DiPoto |
| 2003/0014016 A1 | | 1/2003 | Purdy |
| 2003/0018340 A1 | | 1/2003 | Branch |
| 2003/0191371 A1 | | 10/2003 | Smith et al. |
| 2003/0199884 A1 | | 10/2003 | Davison et al. |
| 2004/0059339 A1 | | 3/2004 | Roehm, III et al. |
| 2004/0133280 A1 | | 7/2004 | Trieu |
| 2004/0143169 A1 | | 7/2004 | Branch et al. |
| 2004/0176665 A1 | | 9/2004 | Branch et al. |
| 2004/0230100 A1 | | 11/2004 | Shluzas |
| 2005/0004593 A1 | | 1/2005 | Simonson |
| 2005/0049664 A1 | | 3/2005 | Harris et al. |
| 2005/0075540 A1 | | 4/2005 | Shluzas et al. |
| 2005/0075644 A1 | | 4/2005 | DiPoto et al. |
| 2005/0080320 A1 | | 4/2005 | Lee et al. |
| 2005/0080443 A1 | | 4/2005 | Fallin et al. |
| 2005/0090899 A1 | | 4/2005 | DiPoto |
| 2005/0101985 A1 | | 5/2005 | Hamada |
| 2005/0137612 A1 | | 6/2005 | Assell et al. |
| 2005/0149035 A1 | | 7/2005 | Pimenta et al. |
| 2005/0159651 A1 | | 7/2005 | Raymond et al. |
| 2005/0192485 A1 | | 9/2005 | Branch et al. |
| 2007/0208227 A1 | | 9/2007 | Smith et al. |
| 2008/0214898 A1 | | 9/2008 | Warren |
| 2009/0018399 A1 | | 1/2009 | Martinelli et al. |

OTHER PUBLICATIONS

Perez-Cruet, Mick, J. et al., "An Update on Endoscopic Thoracic Spinal Surgery: Thoracic Microendoscopic Discectomy", Haid RW Jr, Subach BR, Rodts GE Jr (eds): Advances in Spinal Stabilization Prog Neural Surg., Basel Kruger, 2003, vol. 16 pp. 266-276.

Sandhu, Faheem et al., "Minimally Invasive Surgical Treatment of Lumber Synovial Cysts." Neurosurgery Technique Applications, vol. 54(1):107-112 Jan. 2004.

The Cleveland Clinic, Health Information Center, "Minimally Invasive Spine Surgery: The Benefits", www.spineuniverse.com-displayarticle.php-article1933.html.

Stewart G. Eidelson, M.D., "Spinal Column: An Integral Part of the Human Body" www.spineuniverse.com-displayarticle.php-article2000.html.

Joshua A. Hirsch, M.D., "DISC Nucleoplasty Percutaneous Discectomy" www.spineuniverse.com-displayarticle.php-article2133.html.

Endius Incorporated, "Endius Atavi Atraumatic Spine Surgery System", www.endius.com-atavi.htm.

Steven Richeimer, M.D., "Percutaneous Neuramodulation Therapy (PNT)", http:--www.spineuniverse.com-displayarticle.php-article898.html.

Kevin T. Foley, "Image-Guided Surgery: Space Age Technology Enters the Operating Room", www.spineuniverse.com-displayarticle.php-article756.html.

Fessler, Richard M.D., Ph.D., et al. "Lumbar Discectomy: Minimally Invasive Spine Surgery" www.spineuniverse.com-displayarticle.php-article2005.html.

Caspar, Wolfhard, "The Microsurgical Technique for Herniated Lumbar Disk Operations". Aesculap Scientific Information, 4th Edition.

* cited by examiner

STAND-ALONE ACCESS SYSTEM FOR MINIMALLY INVASIVE SPINAL SURGERY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation application of U.S. patent application Ser. No. 14/665,438, filed Mar. 23, 2015, which is a divisional application of U.S. patent application Ser. No. 13/858,976, filed Apr. 9, 2013, which is a divisional application of U.S. patent application Ser. No. 11/164,831, filed Dec. 7, 2005, the entire disclosure of each of which is hereby expressly incorporated by reference.

FIELD OF THE INVENTION

The invention relates to access systems for conducting minimally invasive spinal surgery, as involving progressively dilating and retracting tissue for exposing a surgical site, and to surgical tooling and procedures associated with such access systems.

BACKGROUND OF THE INVENTION

Minimally invasive spinal surgery, which avoids long incisions and attendant muscle damage, blood loss, and scaring associated with convention spinal surgery, is also credited with shortening recovery periods and reducing postoperative pain, while producing good long-term outcome. Access portals to surgical sites are formed by making short incisions (e.g., less than two centimeters) followed by progressively dilating and retracting intervening tissue. Traditional spinal surgical procedures such as spinal fusion, disc repair, and deformity corrections can be performed through the access portals, which are also referred to as working channels.

Typically, a set of dilators is used to form the access portals, beginning with a guide wire or pin that is inserted through the small incision and advanced until the wire contacts bone in the vicinity of the intended surgical site. Progressively larger tubular dilators are inserted over the guide wire or pin in sequence for stretching muscle and other intervening tissue. A circular retractor replaces the final dilator for holding back the stretched muscle and maintaining a working channel that exposes the intended surgical site. A linkage assembly attached to the surgical table can be used for holding the retractor in place. Surgical tools are inserted through the working channel within the retractor to perform the desired operation. Generally, the surgical site can be viewed directly through the circular retractor. However, an endoscope can be inserted into the working channel to provide enlarged imaging from one or more local perspectives of the surgical site.

US Patent Application Publication 2005/0101985 to Hamada discloses a tapered obturator for replacing the conventional series of dilators. The tapered obturator spreads tissue, first by working its tapered nose to depth and then by temporarily pivoting hemispheric sections apart. After re-closing the hemispheric sections of the obturator, a working tube, which also has hollow hinged hemispheric sections, is inserted over the obturator to secure the dilation gains. The obturator is then re-opened to pivot apart the hollow hemispheric sections of the working tube, further spreading tissue near the surgical site. Lock pins hold the hemispheric sections of the working tube apart, while the obturator is withdrawn to expose a working channel that expands in one dimension approaching the surgical site.

US Patent Application Publication 2004/0230100 to Shluzas discloses a retractor having a wrap-around skirt for similarly expanding a working channel approaching a surgical site. The retractor, while in a generally cylindrical configuration, is inserted over a dilator or dilator assembly that initially reaches the surgical site. The dilator or dilator assembly is then removed to provide access for inserting a scissored expander, which unfurls the wrap-around skirt into a generally conical form. The scissored expander is then removed to expose the surgical site through the expanded retractor.

U.S. Pat. No. 6,206,826 to Matthews et al. discloses a retractor ring formed by concentric inner and outer walls that are partitioned into channels or other openings for holding or guiding surgical tools and ancillary instrumentation. Retractor blades attach by way of clips to the outer wall of the ring. A circular sleeve fits within the inner wall of the ring to provide general surgical access. In between, the partitioned channels of the ring receive ancillary instruments in support of surgical operations. The ring functions as a surgical organizer for arranging surgical instruments within a small access portal and for training surgeons otherwise unaccustomed to working through small working channels to surgical sites.

Conventional retractors, the hinged retractor of Hamada, the wrap-around retractor of Shluzas, and the retractor ring assembly of Matthews et al. maintain fixed access portals to surgical sites. Adjustments to the size or shape of the portals require the participation of additional dilators, obturators, or expanders, which block the working channel until the adjustments are complete. Any change to the size or shape of the portal entrance requires a different retractor or retractor ring.

Other minimally invasive access systems have evolved closer to conventional surgical retractor systems but on a smaller scale. For example, U.S. Pat. No. 5,944,658 to Koros et al. discloses a retractor and distractor system that mounts a set of retractor/distractor blades from an adjustable frame. Two arms of a retractor frame suspend opposing retractor blades. A crossbar linkage between the two arms of the retractor frame includes a gear rack drive for adjusting the spacing between the retractor blades. Two arms of a distractor frame suspend opposing distractor blades at right angles to the two arms of the retractor frame. A similar crossbar linkage between the two arms of the distractor frame adjusts the spacing between the distractor blades. A tilting structure is also provided for pivoting the retractor bales together with their support arms about the remaining retractor frame. Despite the complexity of the frame-based system, the manipulation of individual blades is limited, while the entire system can be unwieldy for use securing the small surgical portals required for conducting minimally invasive surgery.

SUMMARY OF THE INVENTION

My invention responds to a need for more flexibility in the configuration of minimally invasive working channels to surgical sites. Surgical demands vary widely between patients and procedures and can be difficult to accommodate within fixed portals of limited size. New retractor assemblies in accordance with my invention include retractor structures that can be articulated with respect to one another so that the dimensions of the working channels are less constrained in comparison to those of conventional minimally invasive retractor systems. In addition to retractor blades, the new retractor assemblies can include specialized surgical tools, such as dissectors.

One version of the invention as a retractor assembly for conducting minimally invasive surgery includes relatively articulable retractor wings configured around a hollow space for defining a working channel to a surgical site. Slots are formed in the retractor wings, and retractor inserts are received within the slots in positions around the working channel.

The retractor wings preferably include three retractor wings, and the retractor inserts preferably include three retractor inserts receivable within the slots of the retractor wings. The retractor inserts are generally arranged as retractor blades that extend beyond a length of the retractor wings along the working channel. However, the retractor inserts can also be arranged to perform specialized surgical functions. For example, individual retractor inserts can be arranged as or replaced by dissecting tools or other instruments or devices for performing such functions as propagating light to the surgical site, imaging the surgical site, or irrigating or aspirating the surgical site.

Each of the slots preferably has a transverse cross section for receiving the retractor inserts having a similar transverse cross section and has a length that extends parallel to the working channel. Preferably, the slots limit transverse motion of the retractor inserts with respect to the retractor wings while permitting unrestricted longitudinal motion of the retractor inserts with respect to the retractor wings along the lengths of the slots.

One end of at least one of the retractor inserts preferably includes an adaptor for attachment to a holder, which can be arranged as a handle for manipulating the retractor insert or as a linkage for attaching the retractor insert to a surgical table. The handle can be oriented at various angles to the retractor inserts (e.g., straight, 30 degree, or 45 degree angle s). Preferably, all of the retractor inserts include adaptors for inserting the retractor inserts into the slots or for withdrawing the retractor inserts from the slots.

The retractor wings are preferably related by temporary interconnections. The preferred retractor wings have adjacent sidewalls, and the interconnections are formed between the adjacent sidewalls of the retractor wings. The adjacent sidewalls can include mating features for interconnecting the retractor wings. For example, the adjacent sidewalls take the form of joints. Such joints can include mating male and female features between the adjacent sidewalls of the retractor wings for holding the retractor wings in a predetermined configuration. In addition, the adjacent sidewalls can be at least partly formed by beveled surfaces that abut each other to function as compression joints.

The joints preferably permit relative angular motion between the retractor wings about axes occupying a continuum of positions along the working channel. However, the same joints can be arranged to constrain relative axial motion between the retractor wings along the working channel. Compressive forces applied to the retractor wings hold the temporary interconnections between the retractor wings together in the form of compression joints that constrain collapse of the retractor wings into the working channel.

Alternatively, the temporary interconnections between retractor wings can take the form of connecting members such as one or more latches that releasable interconnect adjacent retractor wings. The one or more connecting members can also comprise one or more pins that extend through portions of adjacent retractor wings or one or more connecting members formed by end caps that engage portions of adjacent retractor wings. The connecting members can also include one or more corner fittings that engage portions of adjacent retractor wings. The corner fittings are located between the adjacent sidewalls along the length of the retractor wings.

The retractor wings can be arranged in a form that is expandable in a direction that enlarges the working channel. The preferred retractor inserts include a length that extends along the working channel and a transverse breadth that extends substantially tangent to the working channel. The slots of the retractor wings can be made expandable to receive retractor inserts of enlarged breadth.

For example, the retractor wings can be made of relatively movable parts to enable the slots to expand to receive the retractor inserts of enlarged breadth. Interlocks between the movable parts can be used to hold the slots in an expanded form independently of the enlarged retractor inserts. The slots can have a variable cross-sectional shape to assume at least one dimension of the cross-sectional shape of the retractor inserts when the retractor inserts are inserted into the expandable slots. Retractor wings that are made of a flexible material can also form the expandable slots.

Generally, the retractor wings form a closed shape surrounding the working channel. The closed shape can approximate a polygon. A triangular closed shape is most preferred among the closed shapes because of the inherent stability of the triangular form. At least one of the retractor wings preferably includes a slot with substantially straight walls. The retractor wings with straight-walled slots can be made of two interleaved parts for readily expanding or contracting the straight-walled slots to receive different size retractor inserts. However, the retractor wings can also be fashioned as segments of a more conventional cylindrical form having a substantially circular closed shape.

For performing surgical or retracting functions, one or more of the retractor inserts can extend beyond the retractor wings for more closely approaching or entering the surgical site. The specialized retractor inserts can have different lengths.

Another version of the invention as a retractor assembly for conducting minimally invasive surgery includes at least three retractor blades that are relatively articulable with respect to each other and are configurable for defining a working channel to a surgical site. Each of the retractor blades has a length and inner and outer surfaces joined by two side surface s. The retractor blades are configurable such that the lengths of the retractor blades align in a substantially common direction along the working channel and the inner surfaces of the retractor blades face an interior of the working channel. The side surfaces between adjacent retractor blades are shaped for retaining the retractor blades in a desired configuration surrounding the working channel.

Preferably, the side surfaces of adjacent retractor blades are shaped to form temporary interconnections between the adjacent retractor blades. For example, the side surfaces of adjacent retractor blades can include mating features for temporarily interconnecting the adjacent retractor blades. The mating features can include male and female features formed in the side surfaces of adjacent retractor blades. One side surface of each of the retractor blades can include a male feature and the other side surface of each of the retractor blades can include a female feature.

The adjacent retractor blades preferably contact each other through a range of positions along a common length of the adjacent retractor blades. The mating features of the adjacent retractor blades preferably extend through the range of contact positions. In addition, the mating features preferably remain substantially constant through the range of contact positions.

The side surfaces between adjacent retractor blades can take the form of joints, which can be shaped to permit relative angular motion between the retractor blades over a continuum of positions along the lengths of the retractor blades or to permit relative translation between the contacting portions of adjacent retractor blades. The joints are preferably held together by compressive forces applied to the retractors and prevent the collapse of the retractors into the working channel. For example, the side surfaces between adjacent retractor blades can be formed at least in part as mating bevel surfaces that abut each other to function as compression joints.

The retractor blades preferably include top and bottom ends and include an adaptor mounted adjacent to the top end of at least one the retractor blades. The adaptor can be used to attach a handle to the retractor blades or to participate in attaching the retractor blades to a surgical table.

One or more of the retractor blades can differ from other of the retractor blades. For example, the one retractor blade can be arranged as a dissecting tool or as an instrument for propagating light to the surgical site or for imaging the surgical site. One of the retractor blades can also be arranged for irrigating or aspirating the surgical site.

The individual retractor blades can be replaced for performing different or revised functions. The preferred retractor blades are configurable into closed shape surrounding the working channel. The closed shape can approximate a polygon, but preferably approaches a triangle.

At least one and preferably both of the inner and outer surfaces of the retractor blades have sections that are substantially planar. The total number of retractor blades is preferably limited to three retractor blades so that the retractor blades can be configured in a naturally stable form.

Another version of the invention as a dilator assembly for exposing a surgical site with minimal invasion includes a set of progressively larger dilators for opening a surgical site in stages. Each of the dilators includes an internal surface having an internal cross-sectional shape and an external surface having an external cross-sectional shape. An interim one of the dilators has substantially rounded internal and external cross-sectional shape s. A transitional one of the dilators has an internal surface with a rounded internal cross-sectional shape that substantially matches the rounded external cross-sectional shape of the interim dilator and has an external surface that includes a non-rounded external cross-sectional shape.

Preferably, the external surface of the transitional dilator transitions from a rounded cross-sectional shape at one end to a non-rounded cross-sectional shape at an opposite end. The non-rounded external cross-sectional shape of the transitional dilator is preferably approximately triangular, whereas the rounded internal cross-sectional shape of the transitional dilator is preferably approximately circular. The dilator assembly also preferably includes a retractor assembly having non-rounded internal and external cross-sectional shape s. The set of dilators are removable for exposing the surgical site through a non-rounded working channel bounded by the retractor assembly.

The retractor assembly preferably includes at least one relatively articulable retractor blade for manipulating the surgical site. The retractor assembly can also include relatively articulable retractor wings within which slots are formed. The slots receive retractor inserts within the retractor wings. At least one of the retractor inserts extends beyond the retractor wings toward the surgical site. The retractor inserts can differ from one another for supporting two or more different surgical functions.

The retractor wings are preferably interconnected by joints that permit relative motion between the retractor wings while preserving a working channel to the surgical site. In addition, the retractor inserts are preferably pivotable together with the retractor wings in directions that expand the working channel at the surgical site.

Alternatively, the retractor assembly can also be formed as an assemblage of three or more retractor blades that can be separately manipulated. The blades surround a working channel to the surgical site. Although all of the blades preferably participate in a tissue retraction function, the blades can differ from one another to perform additional functions in support of a surgical operation. For example, the individual blades can be arranged as a dissector, an illuminator, site imager, irrigator, or aspirator. The blades can have different sizes and shapes for performing the different functions. Since the blades define the working channel to the surgical site, the blades are not confined within a fixed space and can be manipulated for adjusting the boundary of the working channel.

Another version of the invention as a method of initiating a minimally invasive surgical procedure includes dilating tissue for forming a working channel to a surgical site and supporting the working channel with a retractor assembly having at least three relatively articulable components that are positioned around the working channel with temporary interconnections bridging adjacent sidewalls of the components. Each of the relatively articulable components is pivotable with respect to the other of the relatively articulable components about a range of different pivot axes.

Preferably, the relatively articulable components have overlapping lengths and the different pivot axes are spaced apart between ends of the overlapping lengths. Each of the relatively articulable components can also be translated with respect to the other relatively articulable components in a direction along the overlapping lengths of the relatively articulable components.

The relatively articulable components preferably include at least three retractor wings that are configured around the working channel to the surgical site. One or more retractor blades can be inserted through the retractor wings in positions that extend beyond the retractor wings toward the surgical site. Each retractor blade together with the retractor wing in which the blade is inserted can be pivoted with respect to other of the retractor wings for adjusting the working channel to the surgical site.

Alternatively, one or more dissecting tools can be inserted through the retractor wings in positions that extend beyond the retractor wings toward the surgical site. Each of the dissecting tools can be pivoted together with the retractor wing in which the tool is inserted with respect to other of the retractor wings for carrying out a dissecting function at the surgical site.

Initially, the slots within the retractor wings can be filled with temporary plugs prior to the step of supporting the working channel with the retractor assembly. The plugs can be replaced within the retractor wings with one or more surgical tools while the retractor wings are in place around the working channel.

The relatively articulable components can also include a plurality of retractor blades having the side surfaces between adjacent retractor blades that are shaped for retaining the retractor blades in a desired configuration surrounding the working channel. Interconnections formed between the side surfaces of the retractor blades can be used to sustain the retractor blades in a stable form surrounding the working channel. Preferably, each of the retractor blades can be both pivoted and translated with respect to other of the retractor blades.

Prior to inserting the retractor assembly, progressively larger dilators can be inserted one over the other for enlarging the working path to the surgical site. Preferably, a transitional dilator having a rounded internal cross sectional shape and a non-rounded external cross-sectional shape is inserted over a smaller dilator having a rounded internal and external cross-sectional shape. The retractor assembly can have a non-rounded internal cross-sectional shape conforming to the non-rounded external cross sectional shape of the transitional dilator and can be inserted over the transitional dilator for defining the working channel to the surgical site.

DETAILED DESCRIPTION OF THE INVENTION

Figure 1:
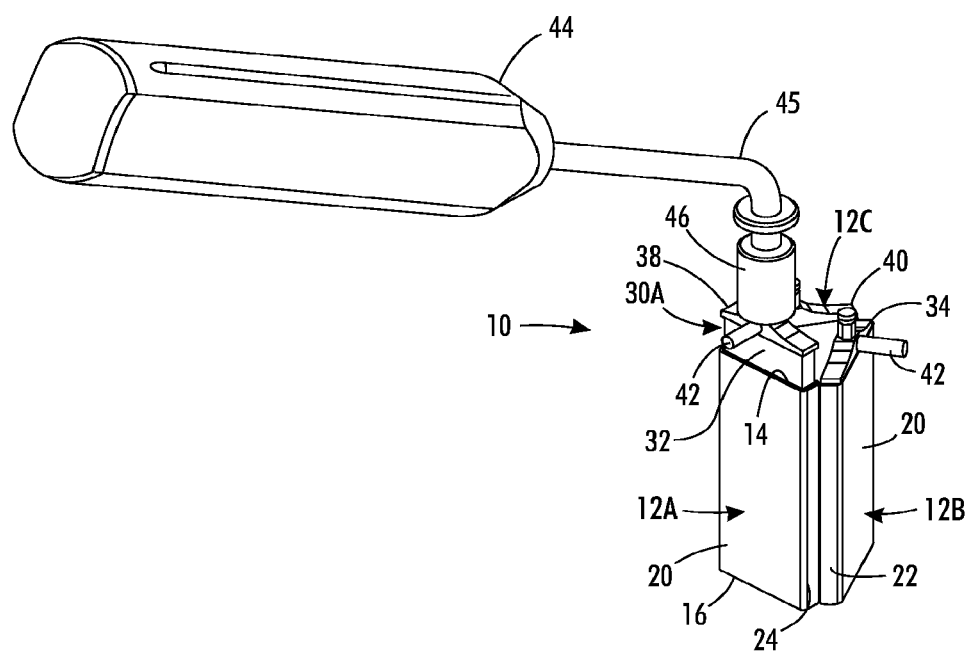
FIG. 1 is a perspective view of a retractor assembly configured from a set of retractor wings and having a handle attached to a retractor insert received within one of the retractor wings.
Figure 2:
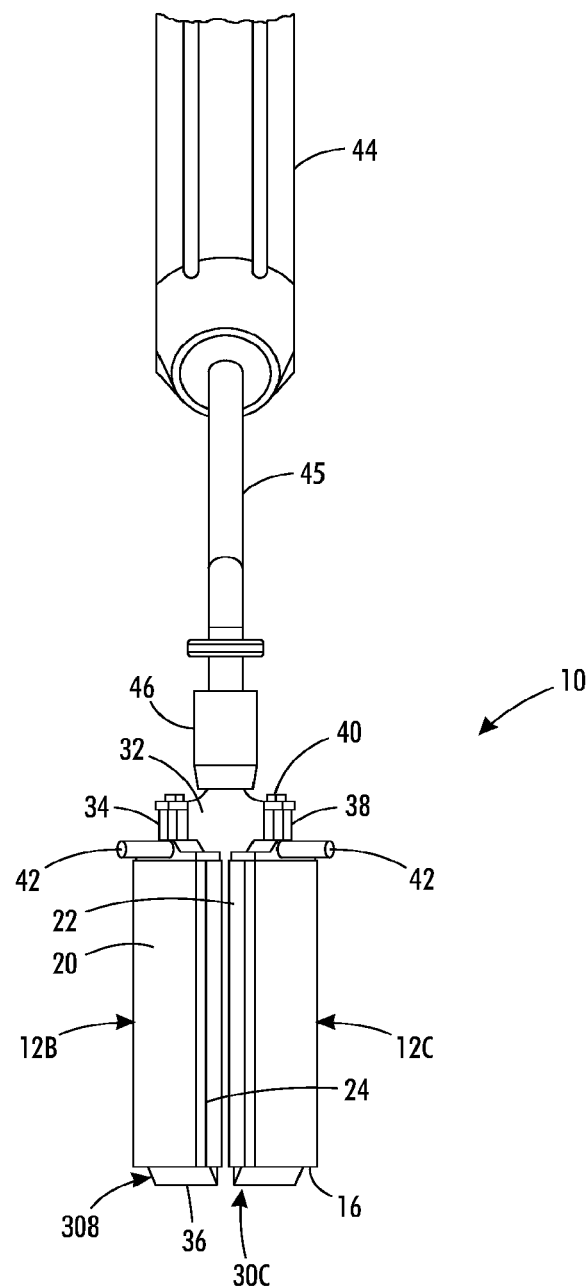
FIG. 2 is a front view of the retractor assembly of FIG. 1.
Figure 3:
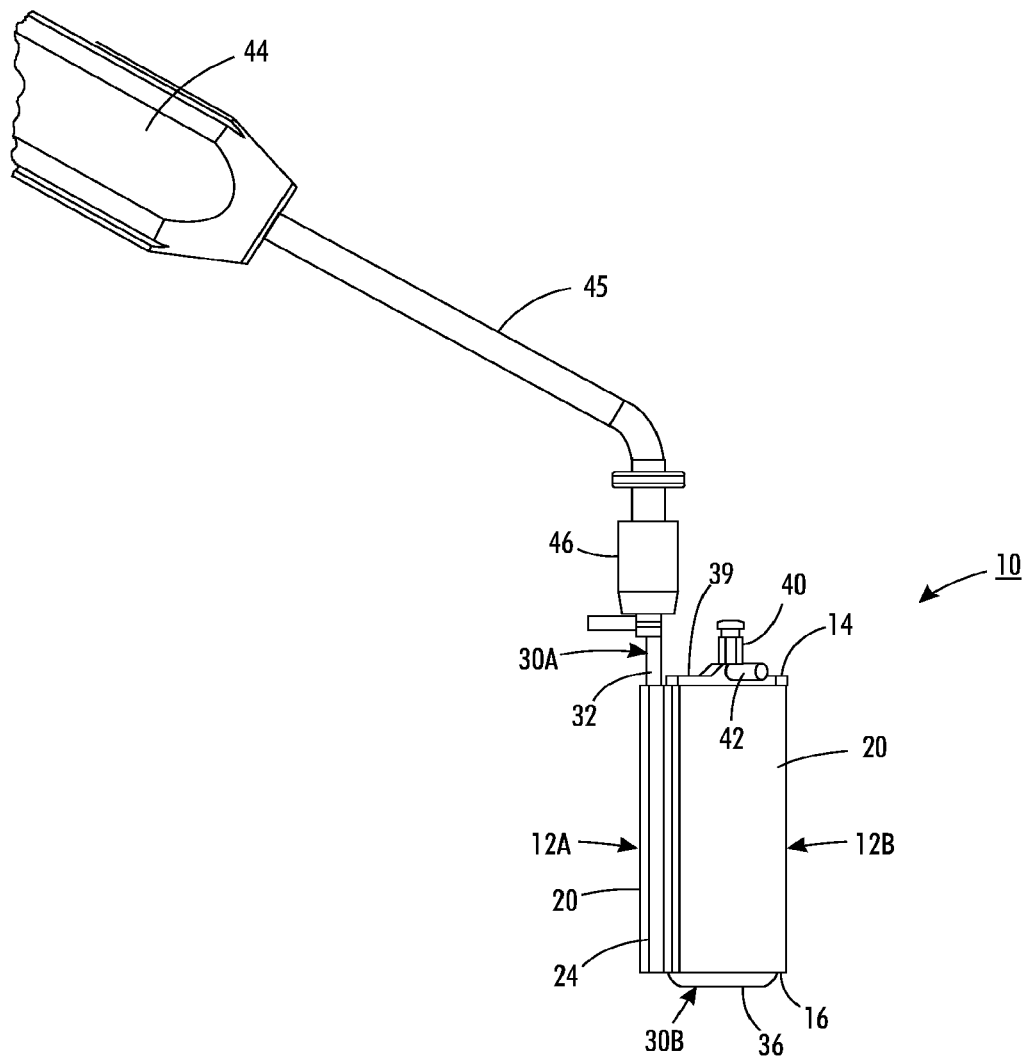
FIG. 3 is a side view of the retractor assembly of FIG. 1.
Figure 4:
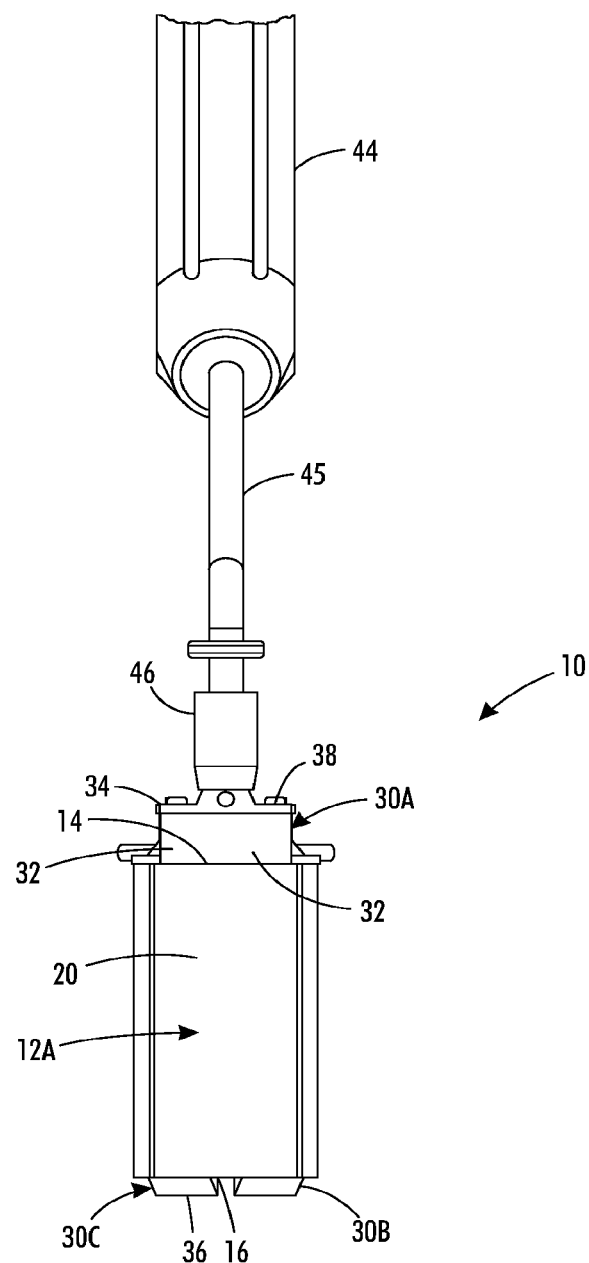
FIG. 4 is a back view of the retractor assembly of FIG. 1.
Figure 5:
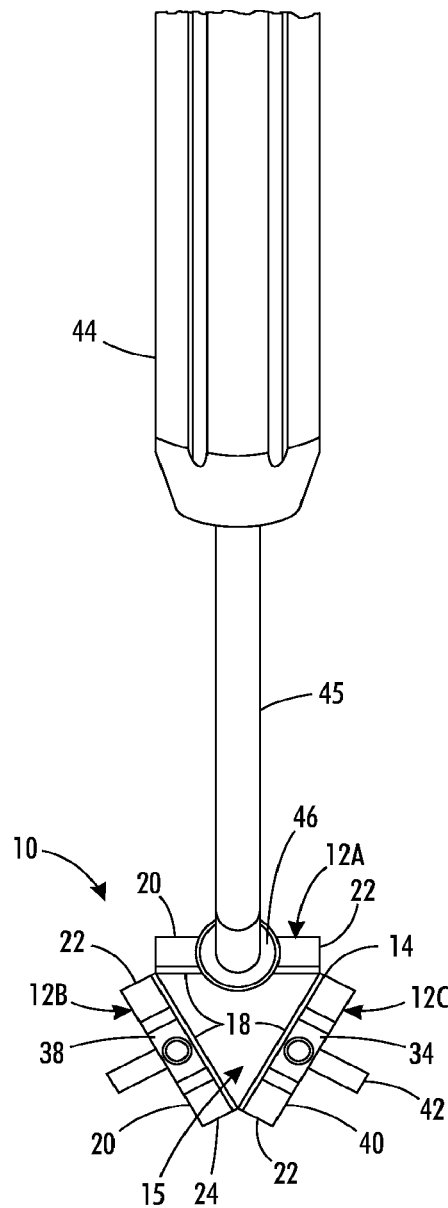
FIG. 5 is a top view of the retractor assembly of FIG. 1.
Figure 6:
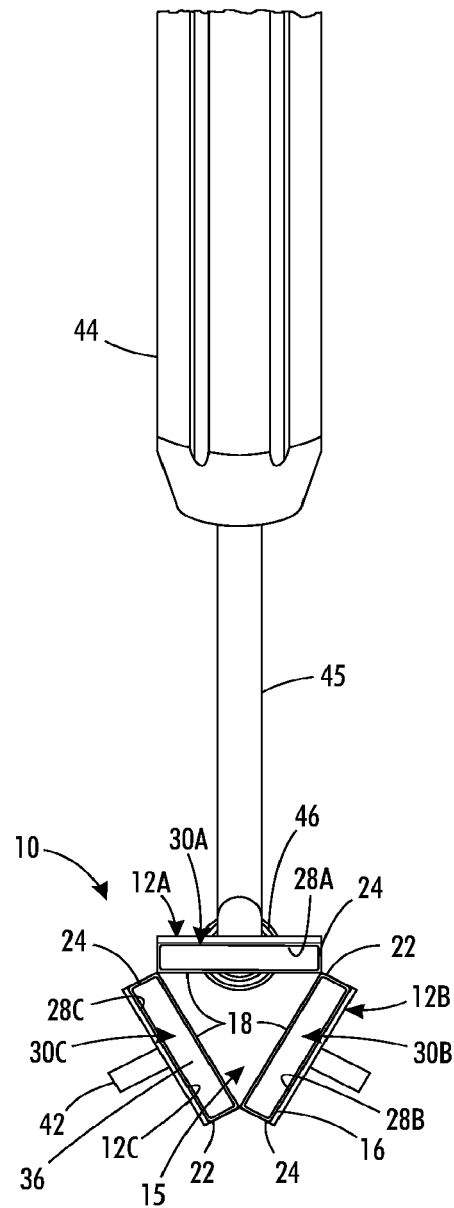
FIG. 6 is a bottom view of the retractor assembly of FIG. 1.

A retractor assembly 10 intended for the practice of my invention is shown in FIGS. 1-6 from various perspectives. Three relatively articulable retractor wings 12A, 12B, and 12C are configured into a triangular shape appropriate for defining a working channel 15 to a surgical site. Each of the retractor wings 12A-C extends a length between top and bottom ends 14 and 16 and includes inner and outer surfaces 18 and 20, joined by opposite side surfaces 22 and 24. For defining the working channel 15, the retractor wings 12A-C are configured so that their lengths are aligned in a common direction along the working channel and their inside surfaces 18 face an interior of the working channel 15. The retractor wings 12A-C are preferably made of metal or resin materials, such as polypropylene resin or stainless steel, aluminum, or titanium metals, that are safe for contact with body tissues.

Slots 28A, 28B, and 28C, which have a generally rectangular cross-sectional shape, extend through the full lengths of the respective retractor wings 12A-C. Received within the respective slots 28A-C, are retractor inserts 30A, 30B, and 30C also having a generally rectangular cross-sectional shape for substantially filling the slots 28A-C.

The retractor inserts 30A-C can also be made of various tissue-compatible materials, selected largely based on their intended function. For example, as plugs that fill the slots 28A-C for performing a dilating function, the retractor inserts 30A-C can be made of resin materials. However, for performing more demanding surgical functions, such as dissection, the retractor inserts 30A-C are preferably made of a steel or strong polycarbonate material. Each of the retractor inserts 30A-C has a slat-shaped body 32 and top and bottom ends 34 and 36. The top ends 34 of the retractor inserts 30A-C include shoulders 38 that functions as stops against top ends 14 of the retractor wings 12A-C. Posts 40 and 42 project orthogonally from the shoulders 38. The posts 40 project in a direction that extends along the length of the retractor inserts 16A-C and, in situ, also project in alignment with the lengths of the slots 28A-C and the intended length of the working channel 15 to the surgical site. The posts 42 project in a direction normal to the wide sides of the slat-shaped bodies 32 and, in situ, also project normal to the outer surfaces 20 of the retractor wings 12A-C and radially of the intended working channel 15.

The posts 40 together with the shoulders 38 provide adapters for attaching the retractor inserts 30A-C to another device such as a handle 44 for individually manipulating the retractor inserts 30A-C or a linkage (not shown) for attaching the retractor inserts 30A-C to a surgical table. For example, the handle 44 is shown in a position for partially inserting or partially retracting the retractor insert 30A to or from the retractor wing 12A. The handle 44 includes a bent shaft 45 and a sleeve 46 that releasably engages the post 40 of the retractor insert 30A. The shaft 45 can be bent at different angle s, including angles of 30 degrees or 45 degrees, or the shaft 45 can be straight as desired to aid in the manipulation of the individual retractor inserts. The posts 42 also provide a ready grip for inserting or removing the retractor inserts 30A-C from their respective retractor wings 12A-C.

Figure 7:
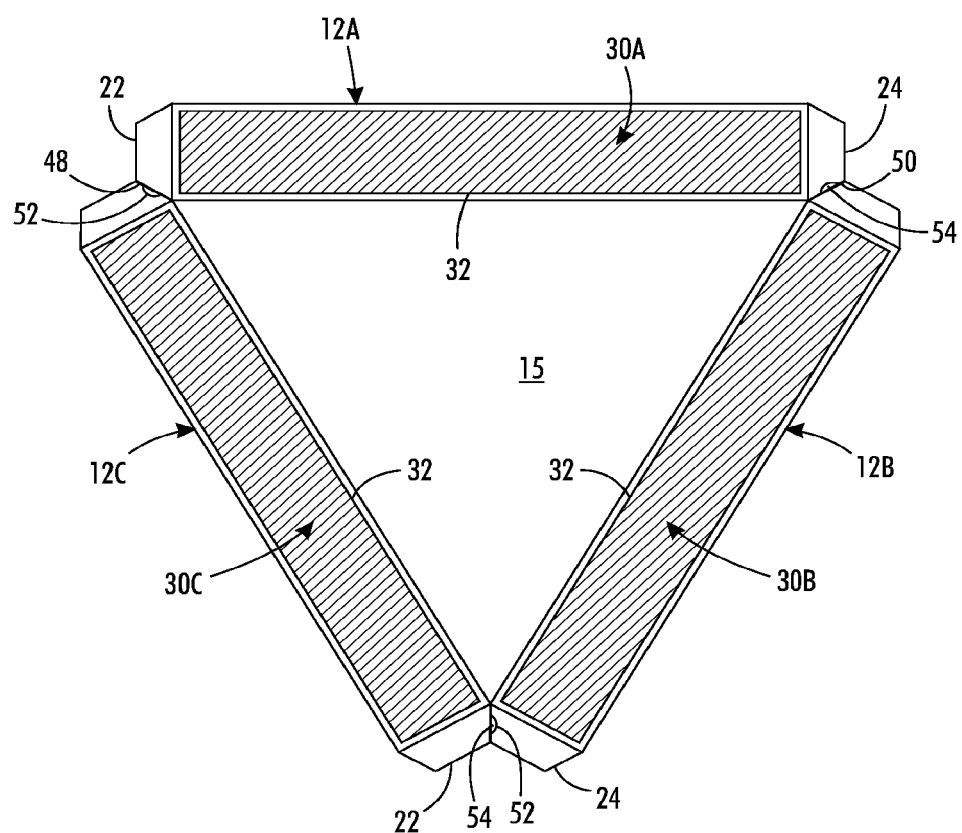
FIG. 7 is a greatly enlarged cross-sectional view through a midsection of the retractor assembly showing retractor inserts arranged for filling slots through the retractor wings.

As shown in the enlarged cross-sectional view of FIG. 7, the retractor wings 12A-C are configurable in a stable triangular form for defining the working channel 15 to the surgical site. The side surfaces 22 and 24 have abutting beveled surfaces 48 and 50 that include male and female mating features 52 and 54, which extend for all or just a part of the length of the retractor wings 12A-C, for temporarily holding the retractor wings 12A-C in the desired triangular configuration. Variations in the male and female features 52 and 54 along the length of the retractor wings can prevent relative axial motion between the adjacent retractor wings, while the adjacent retractor wings are so engaged. Preferably, the male and female mating features 52 and 54 of the bevel surfaces 48 and 50 form compression joints that are drawn together in situ by elastic tissue separated under the force of dilation. The male and female features 52 and 54 are preferably formed in the opposite side surfaces 22 and 24 of each of the retractor wings 12A-C so that all three retractor wings 12A-C have the same overall form. Although the mating features 52 and 54 are depicted as a type of ball and socket joint, a variety of other temporary joint structures can be used including various forms of interlocks, detents, keepers, catches, and splines, or even simple frictional interfaces. The adjacent side surfaces 22 and 24 or the mating features 52 and 54 can be varied along the lengths of the retractor wings 12A-C, such as by adopting an interrupted, stepped, or serpentine form to prevent relative movement between the retractor wings 12A-C along their length.

Figure 8:
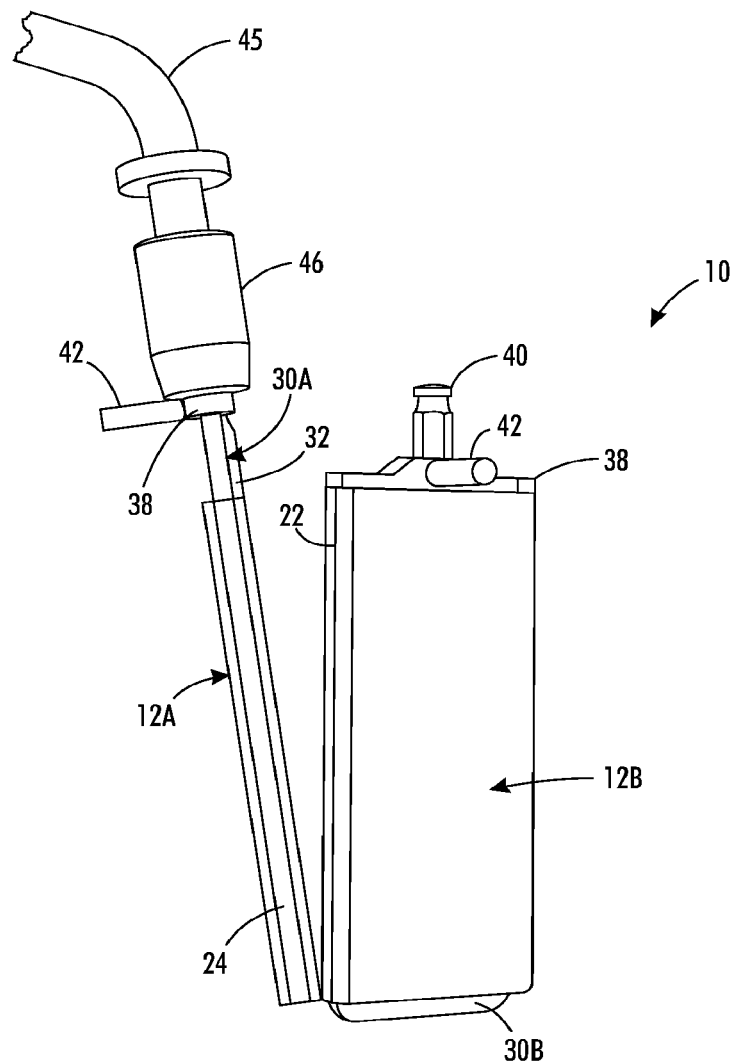
FIG. 8 is a partially enlarged perspective view of the retractor assembly of FIG. 1 showing one of the retractor wings separated from the remaining retractor wings.

The mating features 52 and 58 preferably function to hold the desired triangular configuration under conditions of asymmetric compression and prevent the collapse of the retractor wings 12A-C into the working channel 15. However, the mating feature 52 and 54 do not 23 prevent the retractor wings 12A-C from being individually manipulated such as by being pivoted or otherwise drawn apart from the other retractor wings 12A-C. For example, as shown in FIG. 8, the retractor wing 12A is pivoted apart from the retractor wings 12B and C for enlarging the working channel 15 or for aiding or performing other surgically related functions. The handle 44 is coupled to the post 40 of the retractor insert 30A and pivots the retractor wing 12A via the sliding fit connection of the retractor insert 30A to the retractor wing 12A. The retractor wing 12A or any other of the individual retractor wings 12B or C can be pivoted in other directions or otherwise separated from the other retractor wings to temporarily dilate the working channel 15 or to otherwise aid or perform surgical functions.

The retractor inserts 30A-C are sized largely as fillers for the slots 28A-C within the retractor wings 12A-C for such purposes as preventing tissue from entering the ends 16 of the retractor wings 12A-C as a final or intermediate dilator tool. The ends 36 of the retractor inserts 30A-C are tapered to preliminarily retract tissue during insertion and guide the retractor wings 12A-C along the working channel 15 toward the surgical site.

Figure 9:
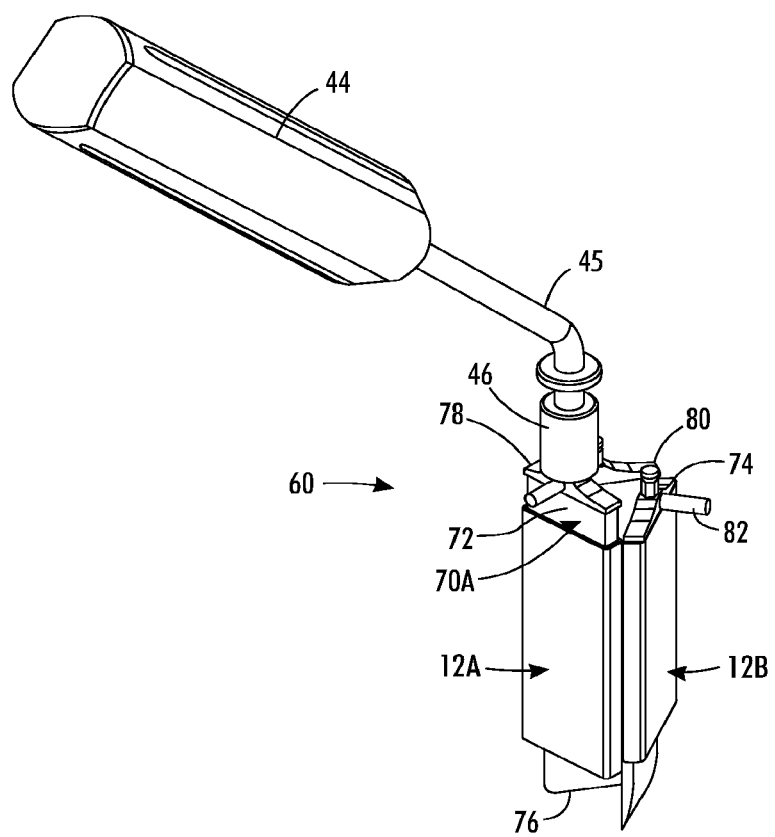
FIG. 9 is a perspective view of another retractor assembly having retractor inserts formed by elongated retractor blades.
Figure 10:
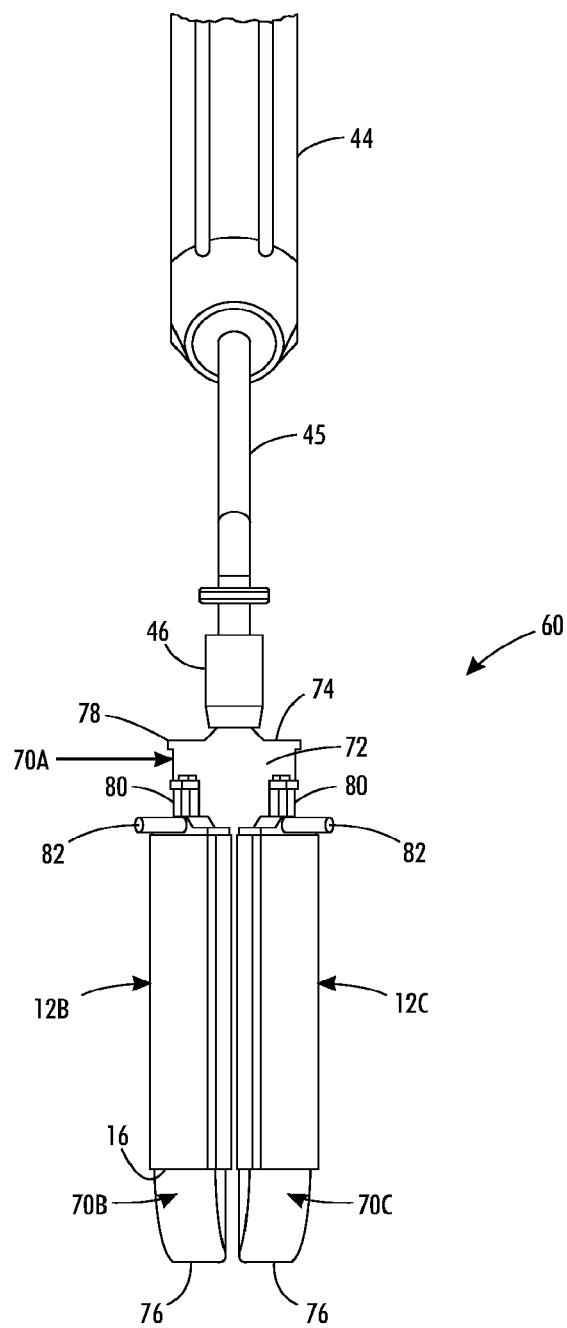
FIG. 10 is a front view of the retractor assembly of FIG. 9.
Figure 11:
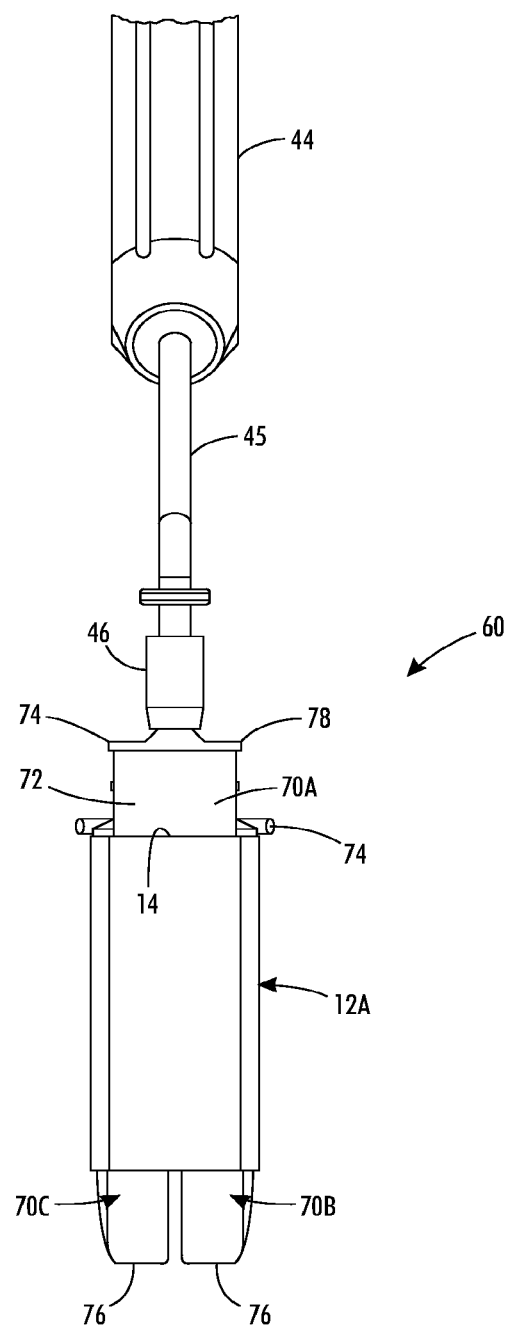
FIG. 11 is a back view of the retractor assembly of FIG. 9.

FIGS. 9-11 illustrate a modified retractor assembly 60 that includes a number of similarly referenced features as the retractor assembly 10 including the three retractor wings 12A-C and the handle 44. However, longer inserts referred to as retractor blades 70A, 70B, and 70C replace the three retractor inserts 30A-C. Like the retractor inserts 30A-C, each of the retractor blades 70A-C has a slat-shaped body 72 and top and bottom ends 74 and 76. The top ends 74 of the retractor inserts 70A-C include shoulders 78 that functions as stops against the top ends 14 of the retractor wings 12A-C. Posts 80 and 82 project orthogonally from the shoulders 78 as adapters or grips for manipulating the individual retractor blades 70A-C. For example the posts 80 are shown coupled to the sleeve 46 of the handle 44. Either post 80 or 82 can be connected to a structure for manipulating the retractor wings 12A-C or to a linkage mechanism for securing the retractor wings 12A-C in place.

The retractor blades 70A-C have a length in the direction of the working channel 15 that exceeds the length of the retractor inserts 30A-C. The ends 76 of the retractor blades 70A-C are preferably formed as tapered edges that can participate in the dilating function or in various surgical functions such as dissection. For example, the edges can be used to clean muscle from limited areas of bone within the surgical site.

Figure 12:
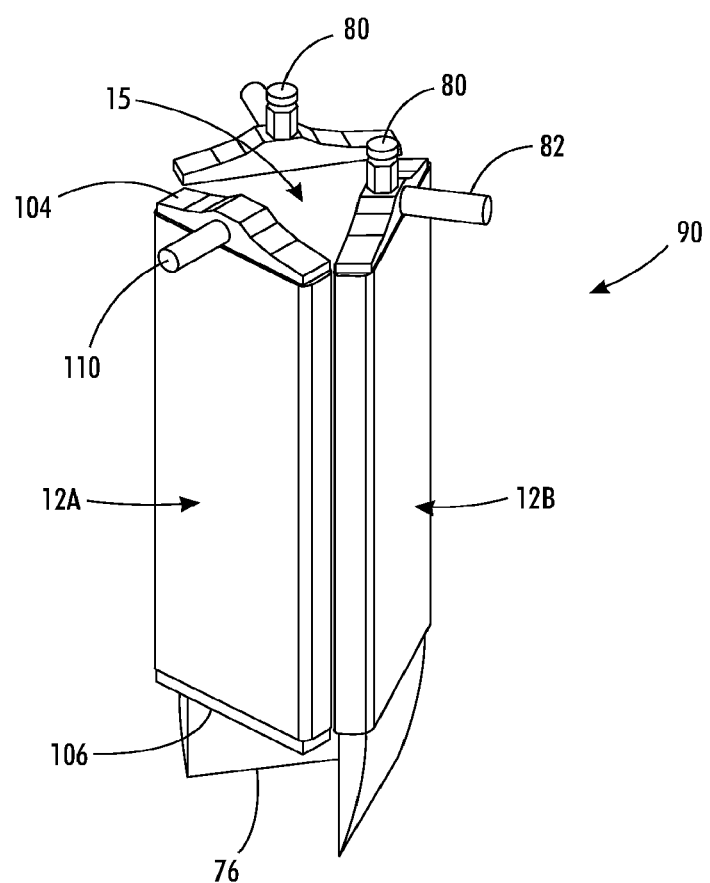
FIG. 12 is a perspective view of a different retractor assembly fitted with a retractor insert modified to function as an illuminator.
Figure 13:
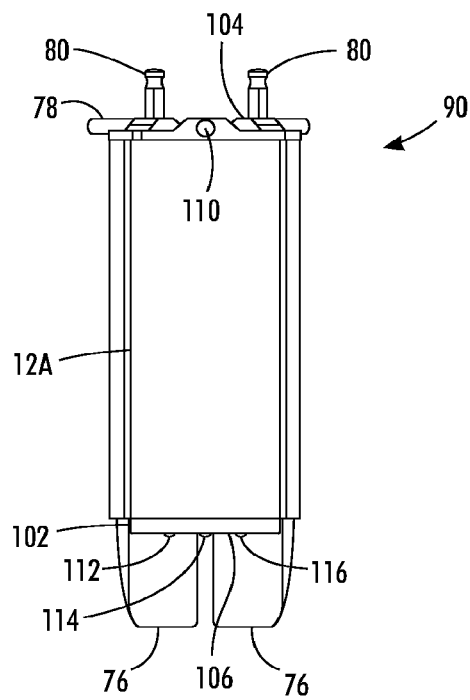
FIG. 13 is a front view of the retractor assembly of FIG. 12.
Figure 14:
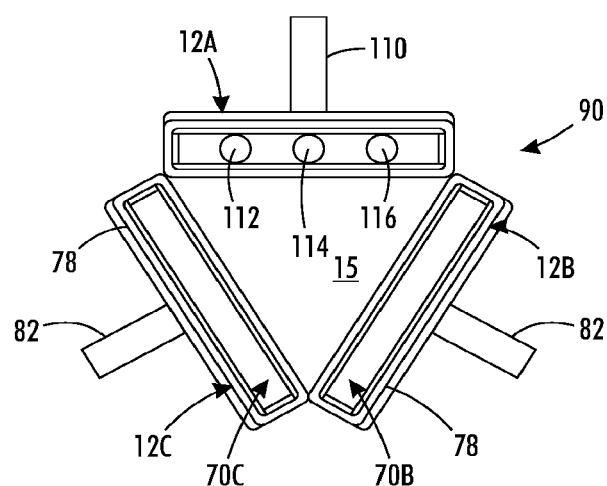
FIG. 14 is a bottom view of the retractor assembly of FIG. 12.

FIGS. 12-14 depict a further modified the retractor assembly 90, which is similar to the retractor assembly 60 except for the substitution of a retractor insert 100A for the retractor blade 70A to provide for illuminating the surgical site. The retractor insert 100A has a slat-shaped body 102 and top and bottom ends 104 and 106. The top end 104 of the retractor inserts 100A includes a shoulder 108 that functions as a stop against the top ends 14 of the retractor wings 12A-C.

In contrast to the earlier embodiments, a post 110 functions as an optical input port for coupling a fiber optic or other light conduit to the retractor insert 100A for connecting the retractor insert to a source of light. Within the slab-shaped body 102, an optical splitter (not shown) divides light coupled at the optical input port (post) 110 into three optical pathways (not shown) that terminate at the bottom end 106 of the retractor insert 100A with optical output ports 112, 114, and 116. Fibers or other waveguides can form the optical pathways for transmitting light from the optical input port (post) 110 to the optical output ports 112, 114, and 116. Fiber ends, lenses, or other optical structures can form the optical output ports 112, 114, and 116 for dispersing light in a desired pattern at the surgical site.

Figure 15:
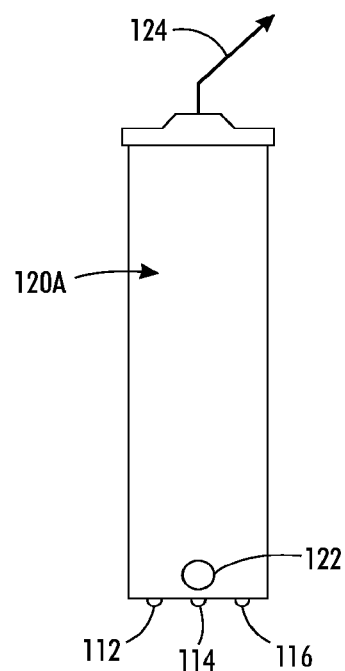
FIG. 15 is a front view of an alternative retractor insert modified to function as both an illuminator and an imager.

A further modified retractor insert 120A is depicted in FIG. 15 for performing an imaging function. In addition to the illuminating features depicted for the retractor insert 100A, the retractor insert 120A incorporates a video camera 122 that is connected by way of a cable 124 to a video monitor or other device capable of significantly enlarging the images captured by the video camera 122. The retractor insert 120A can be manipulated both with respect to and together with a retractor wing, such as the wings 12A-C, for altering the position of the video camera 122 at the surgical site. A zoom lens or other focusing or positioning controls can be incorporated into the video camera 122 to remotely control its operation.

Figure 16:
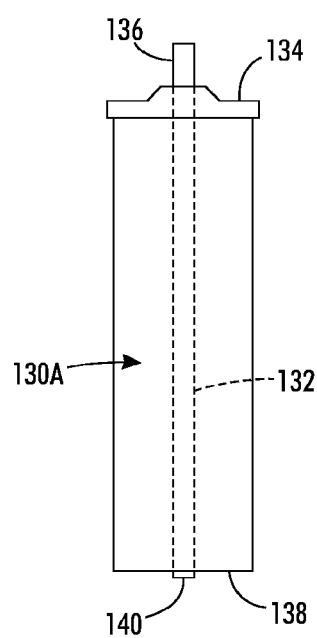
FIG. 16 is a front view of an alternative retractor insert modified to function as an irrigator or aspirator.

Another modified retractor insert 130A shown in FIG. 16 includes an internal conduit 132 beginning at a top end 134 of the insert 130A with a connector port at a post 136 and ending at a bottom end 138 with a nozzle or other opening 140. The conduit 132 can be used for purposes of irrigation or aspiration of the surgical site. Separate conduits can be formed in the retractor insert 130A for separately supporting both irrigation and aspiration functions.

Figure 17:
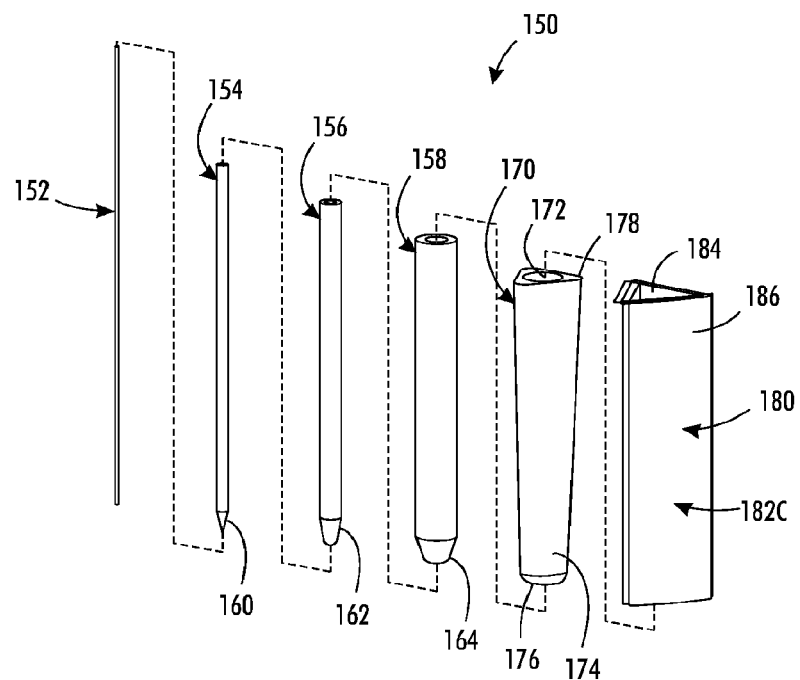
FIG. 17 depicts a dilator system having a set of dilators that progressively vary in both size and shape.
Figure 18:
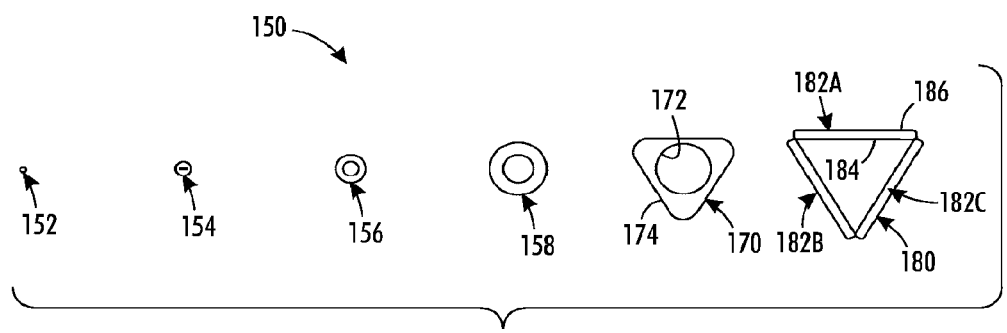
FIG. 18 is a top view of the set of dilators.

A dilating system 150 is shown in FIGS. 17 and 18 of a type that can provide the necessary dilation for inserting the above-described retractor assemblies 10, 60, or 90 along a working channel to a surgical site. The system begins as usual with a fine wire or pin 152 that is inserted through a small incision to the surgical site. Progressively larger tubular dilators 154, 156, and 158 with tape red noses 160, 162, and 164 provide for gradually enlarging the working channel to the surgical site.

The dilator 158, like the smaller tubular dilators 154 and 156, includes an internal surface 166 and an external surface 168, both having rounded (e.g., approximately circular) cross-sectional shapes. A transitional dilator 170 has an internal surface 172 with a rounded (e.g. approximately circular) cross-sectional shape that substantially matches the rounded cross-sectional shape of the external surface 168 of the dilator 158 and has an external surface 174 that transitions from a rounded cross-sectional shape near a tapered nose 176 to a non-rounded (e.g., substantially triangular) cross-sectional shape at an opposite end 178. A retractor assembly 180, which is inserted over the transitional dilator 170, includes an assembly of three retractor wings 182A, 182B, and 182C that collectively form internal and external surfaces 184 and 186 that both exhibit a non-rounded (e.g., substantially triangular) internal cross-sectional shape. The internal surface 184 of the retractor assembly substantially matches the non-rounded (e.g., substantially triangular) cross-sectional shape of the transitional dilator's external surface 174. Once so assembled through an incision to a surgical site, the dilator assembly including dilators 152, 154, 156, 158, and 170 can be removed, leaving the retractor assembly 180 in place for exposing a triangular-shaped working channel to the surgical site.

The transitional dilator 170 can have a non-rounded external surface that extends for all or nearly all of its length. In addition, more than one transitional dilators can be used to progressively vary in cross sectional shape from an initial rounded cross-sectional shape to a non-rounded cross-sectional shape matching the intended internal cross-sectional shape of a retractor assembly. Preferably, the non-rounded cross-sectional shape approaches the form of a polygon having the same number of sides as retractor blades or wings that form the retractor assembly. The corners of the polygonal cross-sectional shape s, particularly the triangular external cross-sectional shapes, are preferably radiused, chamfered, or otherwise blunted to avoid over-stressing surrounding tissue. Accordingly, the polygonal cross-sectional shapes can be recognized by the number of lobes found in the external surfaces of the transitional dilators or the retractor assemblies.

Figure 19:
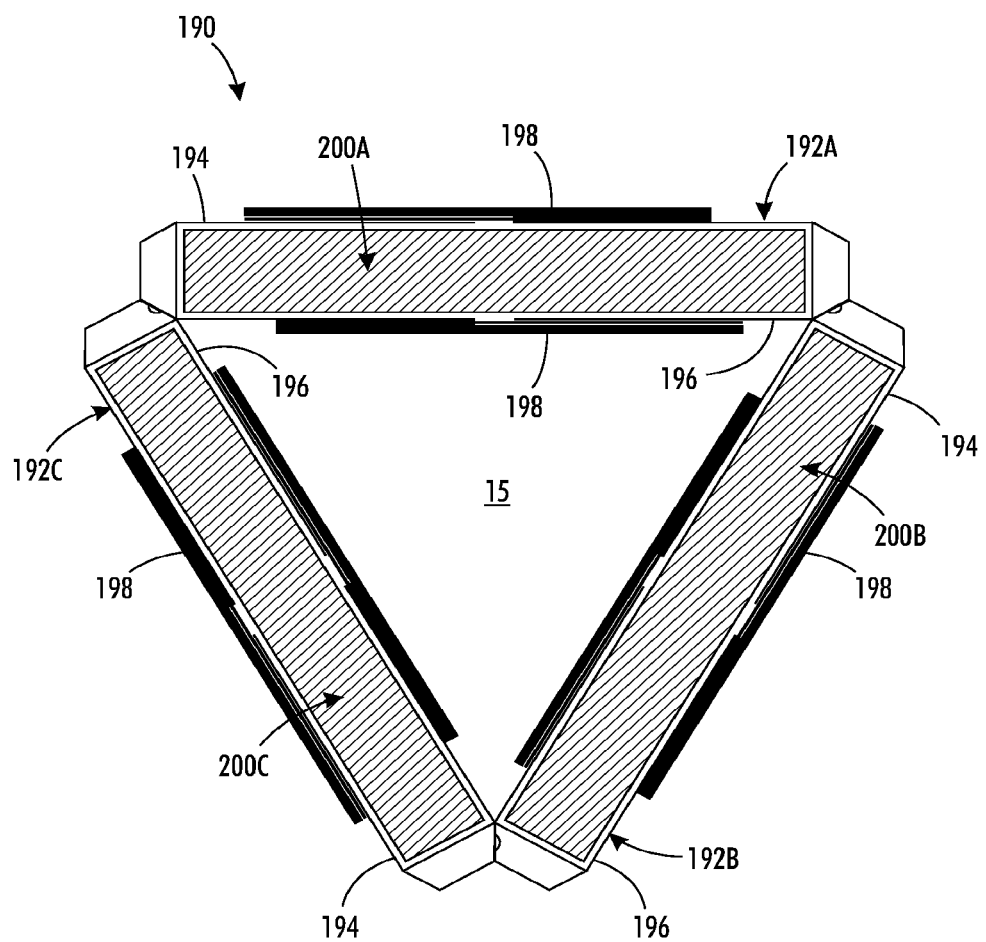
FIG. 19 is a greatly enlarged cross-sectional view of a set of expandable retractor wings holding retractor inserts of a first breadth.
Figure 20:
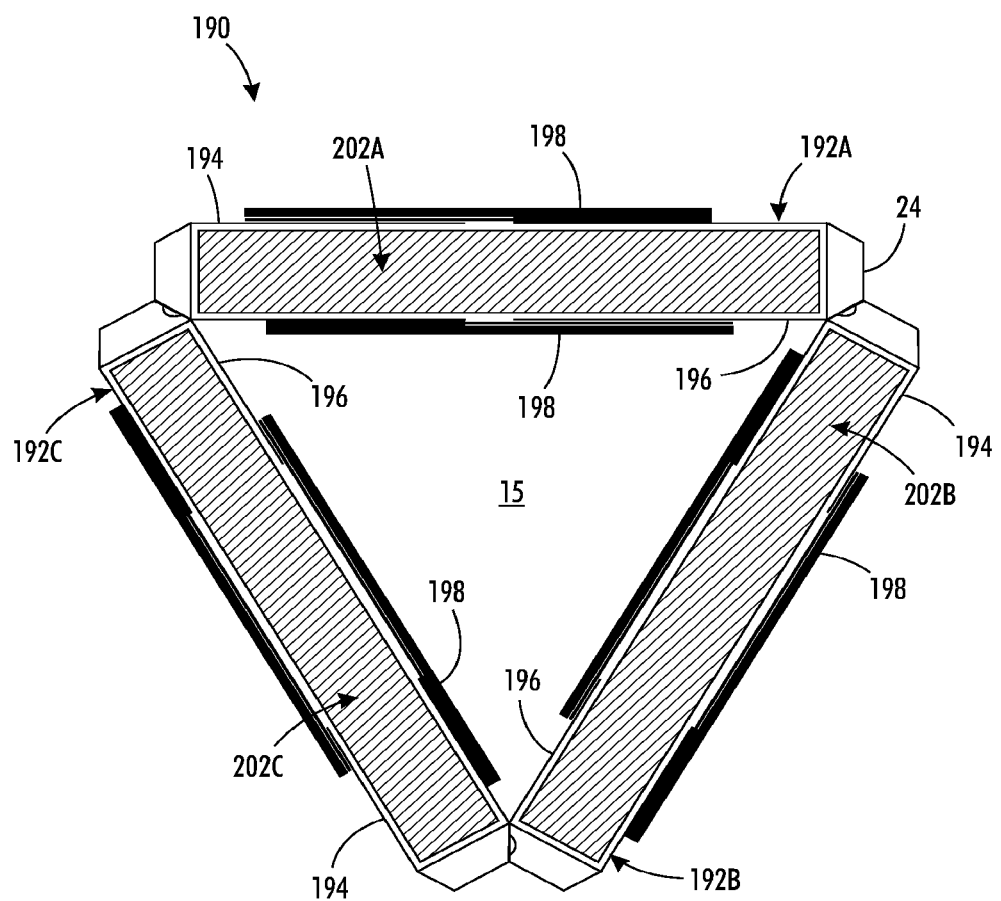
FIG. 20 is a greatly enlarged cross-sectional view of the same set of expandable retractor wings in an expanded condition for holding a retractor insert of a larger breadth.

The retractor wings 182A-C, like the retractor wings illustrated in the preceding embodiments, have a fixed cross-sectional size and shape for receiving retractor inserts having a similar cross-sectional size and shape. However, as shown in FIGS. 19 and 20, a retractor assembly 190 can be configured with a set of retractor wings 192A, 192B, and 192C that are expandable in a direction that enlarges the working channel 15.

Each of the retractor wings 192A-C includes two relatively movable parts 194 and 196 that are interconnected by an expandable joint 198 that allows the relatively movable parts 194 and 196 to expand or contract to accommodate different size retractor inserts 200A, 200B, and 200C or 202A, 202B, or 202C. The expandable joints 198 can take a variety of forms, including interleaving overlaps, for allowing the expansion or contraction of slots 204A, 204B, or 204C within the retractor wings 192A-C. The different size inserts 200A-C or 202A-C can be used to secure the retractor wings 192A-C in various expanded or contracted positions, or the expandable joints 198 can incorporate interlocks, such as catches, keepers, detents, pins, or frictional engagements so that the retractor wings 192A-C can hold their size independent of the retractor inserts 200A-C or 202A-C.

Figure 21:
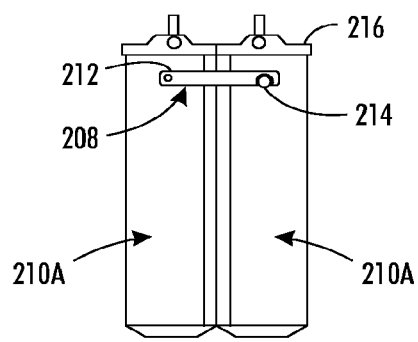
FIG. 21 is a front view of a pair of retractor wings temporarily held together by a latch.

Whether expandable or not, the retractor wings can be temporarily held together in a desired configuration in a variety of ways. For example, FIG. 21 depicts a latching mechanism 208 that can be used for securing adjacent retractor wings 210A and 210B. The latching mechanism 208, which includes a pivot bar 212 associated with the retractor wing 210A and a catch 214 associated with the retractor wing 210B, is located near a top end 216 or the retractor wings 210A-B so as to be readily accessible for locking or unlocking the retractor wings 210A-B together. Other types of latching mechanisms can also be used, including both integral and non-integral structures that extend between adjacent retractor wings and provide releasable connections between the adjacent retractor wings. For example, pins, clasps, hasps, catches, bolts, end caps, and other rigid fasteners can be used, as well as flexible fasteners including elastic bands that encircle part or the entire periphery of the retractor assemblies.

Figure 22:
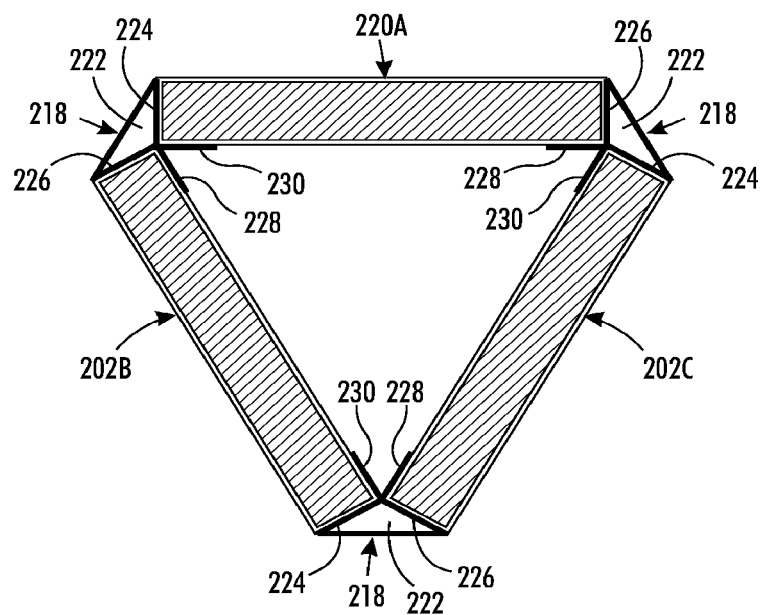
FIG. 22 is a greatly enlarged cross-sectional view of a retractor assembly showing corner fittings for temporarily holding the retractor wings together.

For example, FIG. 22 illustrates another way of temporarily holding retractor wings together by using corner fittings 218 between adjacent pairs of retractor wings 220A, 220B, and 220C. Each of the corner fittings 218 includes a main body 222 that abuts adjacent sidewalls 224 and 226 of the retractor wings 220A-C and two ears 228 and 230 that contact interior surfaces 232 of the retractor wings 220A-C. The corner fittings 218 secure the retractor wings 220A-C in a desired triangular configuration under compression while permitting the retractor wings 220A-C to be individually pivoted or otherwise separated from the remaining retractor wings for performing individual operations.

Figure 23:
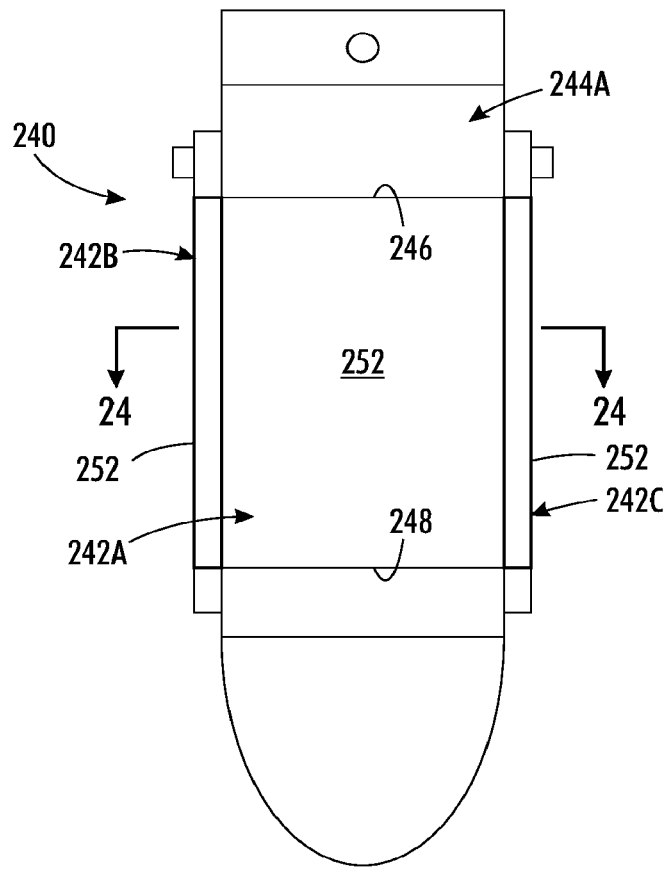
FIG. 23 is a back view of an alternative retractor assembly having an approximately circular closed cross-sectional shape.
Figure 24:
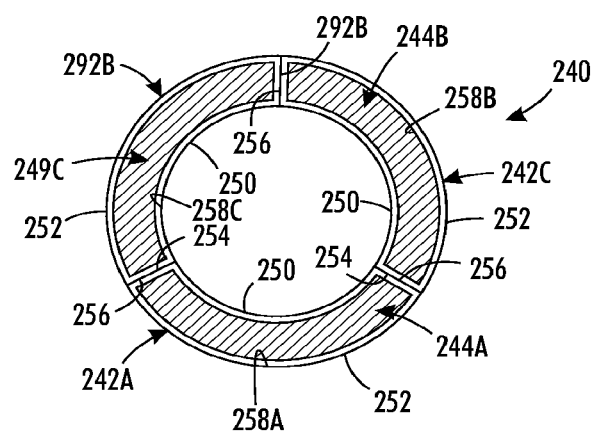
FIG. 24 is a cross-sectional view of the circular retractor assembly taken along line 24-24 of FIG. 23.

An alternative retractor assembly 240 shown in FIGS. 23 and 24 includes in common with the preceding embodiments three retractor wings 242A, 242B, and 242C and three retractor inserts 244A, 244B, and 244C but has an overall circular rather than an overall triangular form. Each of the retractor wings 242A-C extends a length between top and bottom ends 246 and 248 and has an inner surface 250 and an outer surface 252 joined by two side surfaces 254 and 256. The inner and outer surfaces 250 and 252 have concentric arcuate shapes, and the side surfaces 254 and 256 of adjacent retractor wings abut one another along radial lines. Although mating features can incorporated into the sides surfaces 254 and 256 for forming mechanical interlocks, the side surfaces 254 and 256 are arranged for a largely frictional engagement that is intended for retaining the retractor wings 242 A-C in a circular closed form under the influence of anticipated asymmetric compression forces.

Arcuate slots 258A, 258B, and 258C are formed within the respective retractor wings 242 A-C for receiving the retractor inserts 244A-C, which also have arcuate cross sections. The retractor insert 244A differs from the other two inserts 244B and 244C in both length and form for performing a specialized surgical function, such as dissection. The slot 258A allows the retractor insert 244A to be relatively translated along the length of the retractor wing 242A. The frictional interfaces formed by the abutting side surfaces 254 and 256 allow the retractor wing 242A together with the retractor insert 244A to be pivoted or otherwise separated from the adjacent retractor wings 242B and 242C for performing functions at or near the intended surgical site.

The retractor wings can be configured in a variety of overall closed forms for individually supporting retractor inserts having a corresponding variety of different cross-sectional shape s. The cross-sectional shapes of the slots preferably remain constant along the length of the retractor wings. Although the cross-sectional shapes of the retractor 32 inserts preferably match the cross-sectional shapes of the retractor wing slots in which they are received, the cross-sectional shapes of the retractor inserts can vary along their length, particularly at their working ends, to carry out their intended functions.

Figure 25:
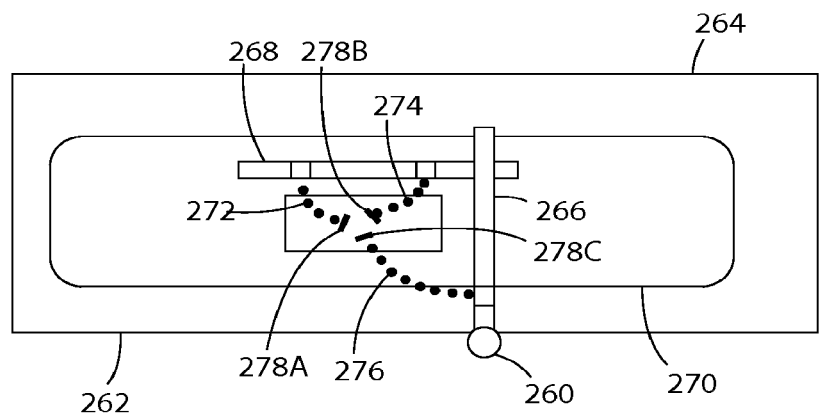
FIG. 25 is a plan view of an operating table showing a frame for securing a set of retractor blades to the table.
Figure 26:
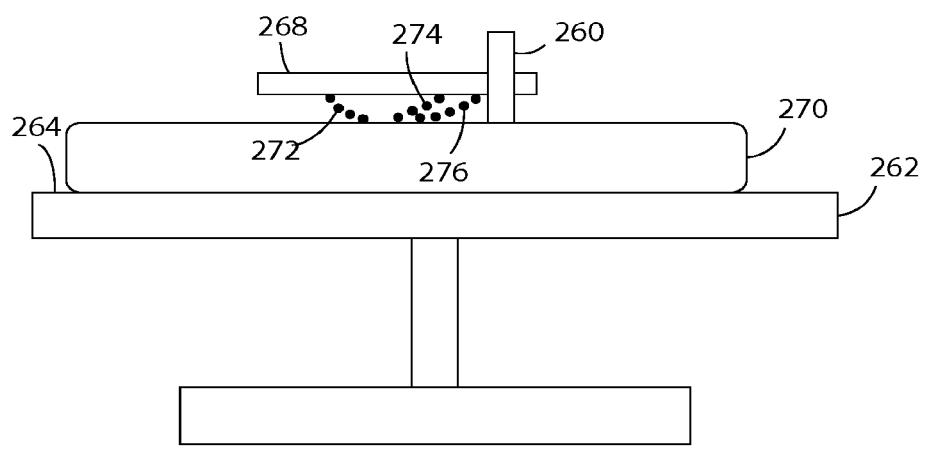
FIG. 26 is a side view of the operating table and frame for securing the retractor blades.

The retractor inserts and with them the retractor wings can be individually secured to a surgical table using conventional framing structure s. FIGS. 25 and 26 illustrate such a surgical setup. A post 260 clamped to a side rail 262 of a surgical table 264 supports adjustable crossbars 266 and 268 in positions cantilevered over a patient 270. Flexible, multilink connector arms 272, 274, and 276 can be manipulated to connect individual retractor blades 278A, 278B, and 278C to the crossbars 266 and 268. Once so connected, the links of the connector arms can be tightened to provide a rigid connection to the crossbars 266 and 268.

Figure 27:
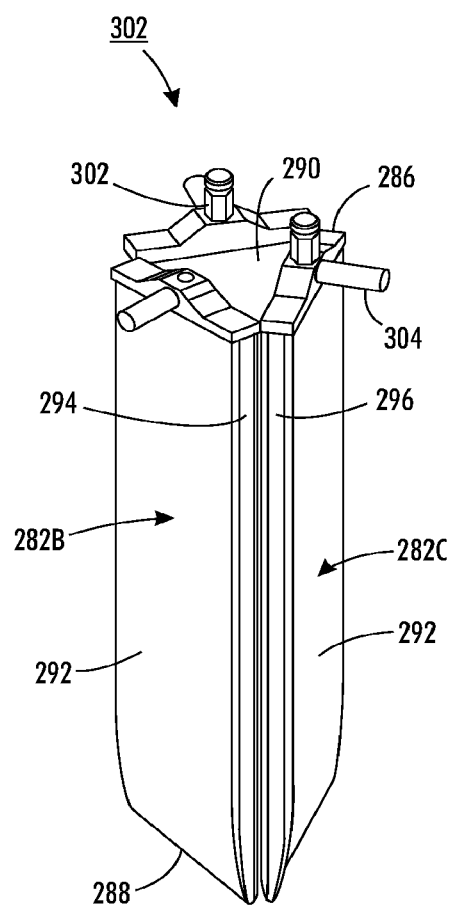
FIG. 27 is a perspective view of a retractor assembly constructed by a set of three retractor blades in a triangular configuration.
Figure 28:
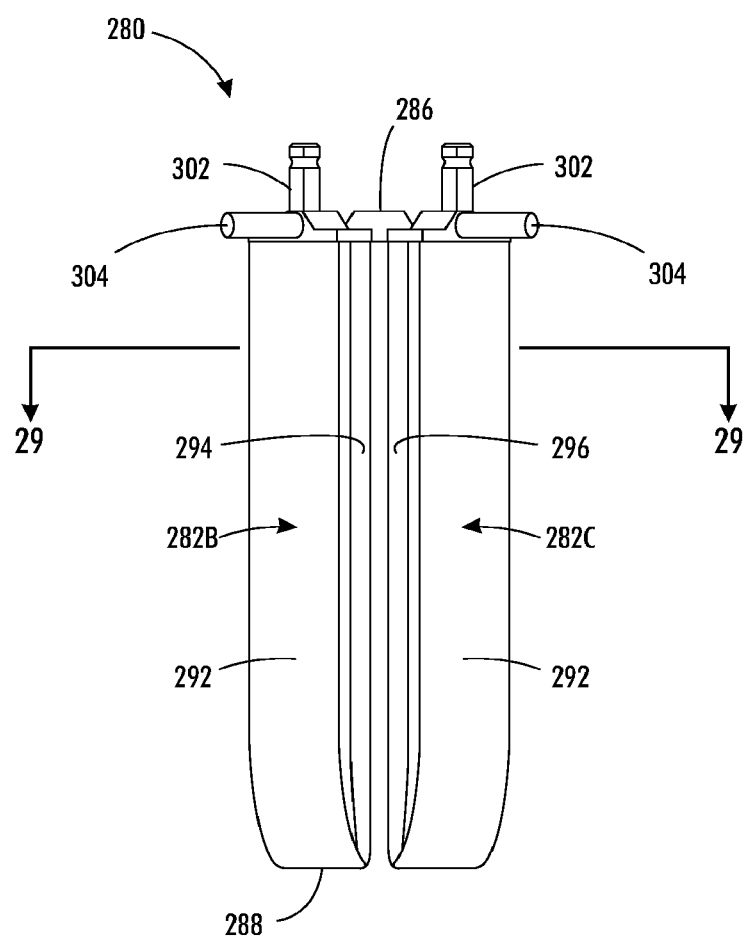
FIG. 28 is a front view of the retractor assembly of FIG. 27.
Figure 29:
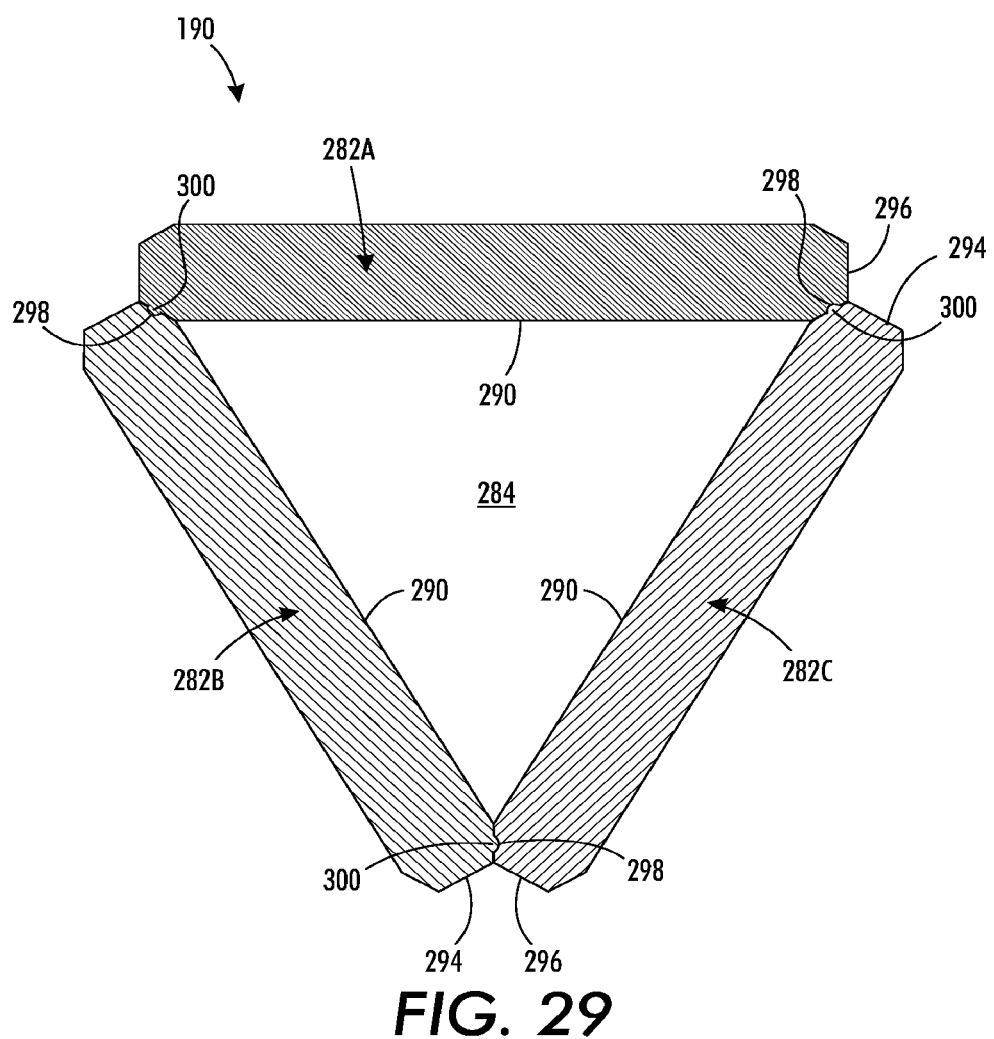
FIG. 29 is an enlarged cross-sectional view of the retractor assembly taken along line 29-29 of FIG. 28.

As shown in FIGS. 27-29, a set of three retractor blades 282A, 282B, and 282C can be configured into a self-supporting retractor assembly 280 for defining a working channel 284 to a surgical site. Each of the retractor blades 282A-C has a length between top and bottom ends 286 and 288 and inner and outer surfaces 290 and 292 joined by two side surfaces 294 and 296. The retractor blades 282A-C are aligned in a common direction along the working channel 284 and their inner surface 290 face an interior of the working channel 284. At least the exposed surfaces of the retractor blades are preferably made of a tissue compatible material such as various metals or resins including polypropylene resin, stainless steel, aluminum, or titanium. The side surfaces 294 and 296 incorporate mating features 298 and 300 for forming joints as temporary interlocks between adjacent retractor blades 282A-C.

Preferably, at least the female features 300 extend uninterrupted along lengths of contact between the adjacent retractor blades 282A-C so that the retractor blades can be readily translated with respect to each other along their respective lengths while maintaining a stable configuration or so that the retractor blades can be easily withdrawn and replaced with another retractor blade of the same or different size, shape, or function. The male features 298 also preferably extend uninterrupted along the lengths of the contact between the adjacent retractor blades 282A-C to allow the retractor blades 282A-C to be more smoothly separated when pivoting or otherwise moving one of the retractor blades 282A-C out of engagement with its adjacent retractor blades. However, localized male features 298 can be used to favor certain pivot positions over others between the adjacent retractor blades 282A-C.

The side surfaces 294 and 296 of the retractor blades 282A-C can be configured in a variety of other ways as shown for the retractor wings of the preceding embodiments, including simple frictional engagements and other types of temporary mechanical interlocks such as detents, keepers, catches, and splines. In addition, temporary connectors similar to those proposed between the retractor wings can be used between the adjacent retractor blades 282A-C including latches, pins, clasps, hasps, catches, bolts, elastic bands, end caps, and corner fittings.

Similar to the retractor inserts of the preceding embodiments, the retractor blades 282A-C include orthogonal posts 302 and 304 that provide adapters for attaching the retractor blades 282A-C to another device such as a handle for individually manipulating the retractor blades 282A-C or a linkage mechanism for attaching the retractor blades 282A-C to a surgical table.

Although the retractor blades 282A-C have a substantially rectangular cross section, the retractor blades can have a variety of different cross-sectional forms, especially such forms as may be desirable for performing specialized surgical tasks such as dissection. The bottom ends 288 of the retractor blades 282A-C can also be shaped according to their intended use. All three of the retractor blades 282A-C can be substantially similar, or the retractor blades can be individually varied in structure, form, or length for accomplishing different surgical or surgical support functions in addition to retraction, including dissection, illumination, imaging, irrigating, or aspirating.

The retractor blades 282A-C can also be varied in number or form to adjust the shape or size of the working channel 284. When configured together as intended, the retractor blades 282A-C complete a closed form, which is preferably triangular. However, the retractor blade assemblies can assume a variety of different closed shapes including polygonal closed forms based on a plurality of retractor blades having substantially straight inner surfaces or even more conventional circular forms based on a plurality of retractor blades having substantially arcuate inner surface s.

Although the invention has been described with respect to a limited number of embodiments, modifications can be made to the various embodiments and other embodiments will be suggested to those of skill in the art in accordance with the overall teachings of the invention. While the invention is particularly suitable for conducting minimally invasive spinal surgery, other minimally invasive surgeries could also benefit from these general teachings, particularly where increased flexibility and functionality of retractor.

What is claimed is:

1. A retractor assembly comprising:
   at least three retractor blades, wherein the at least three retractor blades are relatively articulable with respect to each other and are configurable in a closed shape for defining a working channel to a surgical site,
   each of the retractor blades having a length and inner and outer surfaces joined by two side surfaces,
   the side surfaces between adjacent retractor blades comprising mating features configured to abut each other to temporarily interconnect the adjacent retractor blades when the at least three retractor blades are configured in the closed shape; and
   wherein at least one of the retractor blades is configured to translate relative to the other retractor blades in a direction along its length when the mating surfaces of its side surfaces abut the mating features of the side surfaces of the adjacent retractor blades.

2. The retractor assembly of claim 1, wherein at least one of the retractor blades is configured to be pivoted relative to the other retractor blades.

3. The retractor assembly of claim 1, further comprising a light conduit extending along one of the retractor blades.

4. The retractor assembly of claim 1, wherein at least one of the retractor blades is configured to be manipulated independently from the other retractor blades.

5. The retractor assembly of claim 1, further comprising a handle configured to allow for manipulation of at least one of the retractor blades independently from the other retractor blades.

6. The retractor assembly of claim 1, wherein the retractor blades are expandable to enlarge the working channel.

7. The retractor assembly of claim 1, wherein the at least three retractor blades comprise three retractor blades and the closed shape is generally triangular.

8. A retractor system comprising the retractor assembly of claim 1 and at least one dilator.

\* \* \* \* \*